United States Patent [19]

Herweck et al.

[11] Patent Number: 4,988,342

[45] Date of Patent: Jan. 29, 1991

[54] IMPROVED FLUID RECOVERY SYSTEM

[75] Inventors: Steve A. Herweck, Nashua; Theodore Karwoski, Hollis, both of N.H.

[73] Assignee: Atrium Medical Corporation, Hollis, N.H.

[21] Appl. No.: 255,764

[22] Filed: Oct. 11, 1988

Related U.S. Application Data

[63] Continuation-in-part of Ser. No. 20,449, Mar. 2, 1987, abandoned.

[51] Int. Cl.$^5$ .............................................. A61M 1/00
[52] U.S. Cl. .......................................... 604/321; 604/4
[58] Field of Search ........................................ 604/4–6, 604/317, 319–321; 137/205

[56] References Cited

U.S. PATENT DOCUMENTS

| | | | |
|---|---|---|---|
| 2,886,035 | 5/1959 | Loutz | 128/272 |
| 3,100,490 | 8/1963 | Desautels | 128/350 |
| 3,115,138 | 12/1963 | McElvenny et al. | 128/278 |
| 3,363,626 | 1/1968 | Bidwell et al. | 128/276 |
| 3,363,627 | 1/1968 | Bidwell et al. | 128/276 |

(List continued on next page.)

FOREIGN PATENT DOCUMENTS

| | | |
|---|---|---|
| 0112641 | 7/1984 | European Pat. Off. |
| 2148331 | 4/1972 | Fed. Rep. of Germany |
| 2351709 | 5/1974 | Fed. Rep. of Germany |
| 2141933 | 1/1985 | United Kingdom |

OTHER PUBLICATIONS

POSTOP Advertisement.
RECEPTASEAL Advertisement.
COMPACT 2000 Advertisement.
FENWAL Laboratories Advertisement.
Voegele et al., "An Improved Method for Collection of Shed Mediastinal Blood for Autotransfusion".
Pleur-Evac Advertisement, "Autotransfusion System" (1986).
Bentley CATR Advertisement "Bentley CATR Cardiotomy/Autotransfusion Reservoir System".
Madden et al., RN, pp. 50–53 (Dec. 1983), "Autotransfusion: Now It's Saving Lives in the ED".

Cosgrove et al., The Annuals of Thoracic Surgery, vol. 40, No. 5, pp. 519–520 (Nov. 1985), "An Improved Technique for Autotransfusion of Shed Mediastinal Blood".
Cordell et al., "An Appraisal of Blood Salvage Techniques in Vascular and Cardiac Operations".
Engelsher, Surgery, vol. 61, No. 2, pp. 196–199 (Feb. 1967), "A New Underwater Suction Drainage Unit".
Schaff et al., The Journal of Thoracic and Cardiovascular Surgery, vol. 75, No. 4, pp. 632–641 (Apr. 1978), "Autotransfusion of Shed Mediastinal Blood After Cardiac Surgery".
Johnson et al., The Annuals of Thoracic Surgery, vol. 36, No. 2, pp. 173–179 (Aug. 1983), "The Efficacy of Postoperative Autotransfusion in Patients Undergoing Cardiac Operations".

Primary Examiner—Randall L. Green
Assistant Examiner—Randy Shay
Attorney, Agent, or Firm—Lahive & Cockfield

[57] ABSTRACT

A thoracic cavity drainage device includes a first vessel having a plurality of chambers one of which is a regulated drainage chamber, and a separate transfer vessel which receives fluid collected in the drainage chamber of the first vessel. The chambers of both vessels are interconnected in a series by fluid passageways which cooperate to maintain a uniform range of suction in the drainage chamber while preventing passage of water into the drainage chamber and permitting a different level of suction in the transfer vessel. This operation is effective despite relatively large pressure and vacuum impulses caused by stripping of drainage lines, patient coughing, and the like, and despite discrete changes in the physical configuration of the system caused by disconnection of the transfer vessel, connection of the transfer vessel to an infusion line or the opening or closing of fluid lines and ports. A novel transfer vessel empties the drainage device and provides gravity reinfusion of the collected fluids. A mechanism within the transfer vessel provides an effective suction without vacuum connections or pressure regulating adjustments.

26 Claims, 12 Drawing Sheets

U.S. PATENT DOCUMENTS

| | | | |
|---|---|---|---|
| 3,545,440 | 12/1970 | Mishkin et al. | 128/276 |
| 3,552,395 | 1/1971 | Bidwell et al. | 128/276 |
| 3,559,647 | 2/1971 | Bidwell et al. | 128/276 |
| 3,680,560 | 8/1972 | Pannier et al. | 128/276 |
| 3,683,913 | 8/1972 | Kurtz et al. | 128/276 |
| 3,757,783 | 9/1973 | Alley | 128/277 |
| 3,809,085 | 5/1974 | Bidwell et al. | 128/275 |
| 3,830,238 | 8/1974 | Kurtz et al. | 128/275 |
| 3,853,128 | 12/1974 | Kurtz et al. | 128/275 |
| 3,866,608 | 2/1975 | Reynolds et al. | 128/276 |
| 4,006,745 | 2/1977 | Sorenson et al. | 128/214 R |
| 4,015,603 | 4/1977 | Kurtz et al. | 128/276 |
| 4,018,224 | 4/1977 | Kurtz et al. | 128/276 |
| 4,033,345 | 7/1977 | Sorenson et al. | 128/214 R |
| 4,047,526 | 9/1977 | Reynolds et al. | 128/214 R |
| 4,105,031 | 8/1978 | Kurtz et al. | 128/276 |
| 4,112,948 | 9/1978 | Kurtz et al. | 128/276 |
| 4,129,129 | 12/1978 | Amrine | 128/214 R |
| 4,141,361 | 2/1979 | Snyder | 128/278 |
| 4,346,703 | 8/1982 | Dennehey et al. | 128/213 A |
| 4,402,687 | 9/1983 | Denty et al. | 604/319 |
| 4,424,053 | 1/1984 | Kurtz et al. | 604/4 |
| 4,430,085 | 2/1984 | Ahrens | 604/321 |
| 4,439,188 | 3/1984 | Dennehey et al. | 604/283 |
| 4,439,189 | 3/1984 | Sargeant et al. | 604/317 |
| 4,439,190 | 3/1984 | Protzmann et al. | 604/319 |
| 4,443,220 | 4/1984 | Hauer et al. | 604/408 |
| 4,445,884 | 5/1984 | Kurtz et al. | 604/4 |
| 4,460,354 | 7/1984 | Weilbacher et al. | 604/73 |
| 4,519,796 | 5/1985 | Russo | 604/319 |
| 4,529,402 | 7/1985 | Weilbacher et al. | 604/133 |
| 4,540,413 | 9/1985 | Russo | 604/320 |
| 4,559,035 | 12/1985 | Benjamin et al. | 604/73 |
| 4,601,715 | 7/1986 | Olson | 604/321 |
| 4,605,400 | 8/1986 | Kurtz et al. | 604/319 |
| 4,631,050 | 12/1986 | Reed et al. | 604/4 |
| 4,660,354 | 4/1987 | Lancaster et al. | 53/469 |
| 4,664,652 | 5/1987 | Weilbacher | 604/133 |
| 4,767,417 | 8/1988 | Boehringer et al. | 604/31 |
| 4,781,707 | 11/1988 | Boehringer et al. | 604/317 |
| 4,838,872 | 6/1989 | Sherlock | 604/321 |

IMPROVED FLUID RECOVERY SYSTEM

This application is a continuation-in-part of co-pending U.S. application Ser. No. 020,449, filed Mar. 2, 1987, aband., entitled "Chest Drain Device with Means for Recovering Body Fluid".

BACKGROUND OF THE INVENTION

This invention relates to drainage apparatus, and more particularly to apparatus for draining fluids such as blood from a body cavity and for the reuse of such fluids.

Blood recovered from a patient's body cavity (autologous blood) offers significant advantages over blood from other humans (homologous blood). Autologous blood reduces the risk of adverse reactions and transmission of infectious disease, has near normal oxygen carrying capacity and pH, conserves blood supplies, provides a readily available source of compatible blood; and provides cost savings. For these reasons, the practice of reinfusing autologous blood, known as autotransfusion, is expanding rapidly.

Autotransfusion may be used in the emergency room setting to recover blood lost through chest trauma; in the operating room setting to recover blood shed during surgery; or in the intensive care setting to recover shed mediastinal blood following cardiac or other surgery.

Various devices have been developed to drain and collect fluids such as blood from a body cavity for subsequent autoinfusion. The following U.S. patents illustrate prior art developments in drainage and/or autoinfusion devices.

3,559,647 Bidwell et al
3,683,913 Kurtz et al
3,853,128 Kurtz et al
4,018,224 Kurtz et al
4,112,948 Kurtz et al
4,443,220 Hauer et al
4,540,413 Russo
4,605,400 Kurtz et al In U.S. Pat. No. 3,853,128, for example, there is disclosed a drain apparatus of one piece unitary construction. The device includes a collection chamber for collecting fluids from a body cavity, a water seal chamber for preventing passage of air from the atmosphere into the body cavity, and a manometer chamber for regulating the degree of vacuum in the system. The collection chamber is connected by a thoracotomy tube to the patient's pleural cavity. The device is connected to a suction pump and the amount of liquid in the manometer chamber determines the degree of vacuum imposed. A valve mechanism is provided in the water seal chamber to permit the outflow of gases from the apparatus in the event of a sudden increase in pressure in the device, such as may occur when the patient coughs.

One difficulty encountered with the prior art devices is that no provision is made for autoinfusing simultaneously with draining. A device which would allow autotransfusion simultaneously with draining would have significant advantages over prior art devices, especially in the emergency room and operating room settings. Elimination of time-consuming intervening steps between collection, transfer of blood, and autotransfusion would streamline the autotransfusion tasks of medical personnel and enhance the utility of autotransfusion.

The prior art drainage devices generally cannot be used to simultaneously collect blood from the pleural cavity and autotransfuse, because there is no provision in prior art devices for automatic regulation of negative pressure during autotransfusion. During autotransfusion, as fluid exits the collection chamber, remaining fluid volume drops and pressure negativity increases. It is important to maintain pressure negativity within a relatively narrow range to keep bleeding to a minimum and to prevent damage to intrathoracic tissue.

One approach to the solution to this problem is to provide a chamber comprising a collapsable bag whose volume can change as required. See U.S. Pat. No. 4,443,220. Such blood bags may be removed from the drainage device when full and placed on a stand to effect reinfusion, but these devices are incapable of simultaneous drainage and reinfusion. Another approach is to provide a mechanical pressure regulating mechanism in communication with a collection chamber which functions to regulate the subatmospheric pressure in the collection chamber independent of the chamber's effective volume. See U.S. Pat. No. 4,540,413. Such mechanical pressure regulating mechanisms are costly and often unreliable.

The relative underpressures suitable for drainage of the thoracic cavity are in the range of several centimeters of water, representing a pressure difference of well under 0.01 atmospheres. However, the drainage tube from a patient may itself have a significant volume; as a result, the process of "stripping" the tube to clear its lumen by forcing blockages along the tube may introduce substantial fluctuation in pressure into the drainage vessel. Further, the placing of a separate collection vessel in the suction drainage system alters system volume. For these reasons, the combination of known drainage devices with a separate fluid collection chamber for collecting a portion of fluid for reinfusion cannot be expected to maintain a uniform suction at the desired low level. Moreover, known system for fluid collection are not adapted for simultaneously both draining fluids and transferring the desired fluids into the circulatory system.

There accordingly exists a need for a reliable, inexpensive, simple to use, disposable device which allows simultaneous collection and autoinfusion of fluids such as blood while providing dependable regulation of the negative pressure applied to the collection chamber, and which can be used intraoperatively or post operatively.

SUMMARY OF THE INVENTION

The present invention provides a disposable unitary structure for sterile collection of fluids from the thoracic cavity of a patient, and for simultaneous reinfusing such fluids back to the circulatory system of the patient. The apparatus comprises a rigid collection chamber for receiving fluids from the pleural cavity, a U-shaped water seal chamber for preventing unhindered passage of air from the atmosphere into the body cavity, and optionally a manometer chamber for maintaining a selected subatmospheric pressure range in the collection chamber. The collection chamber has three ports: the first port is adapted for connection to a tube for drawing fluids from the pleural cavity or a wound or opening into the collection chamber; the second port communicates with the water seal chamber; and the third port, controlled by a valve, seal or diaphragm is adapted for connection with an infusion pump or separate reinfusion or transfer vessel for delivering fluids collected in the collection chamber into the circulatory system of the patient.

The device includes means for admitting air into the collection chamber when collection chamber pressure drops below a selected subatmospheric level, such as might occur during reinfusion of fluids through the third port. The various means for maintaining an underpressure condition, such as the water seal and manometer, are each configured to have a relatively broad and continuous response to pressure fluctuations. The device is thereby operable to maintain a selected subatmospheric pressure range in the collection chamber during outflow of collected fluid, and to permit reinfusion of fluids from the collection chamber simultaneously with drainage from the pleural or other body cavity into the collection chamber.

In a preferred embodiment, this function is provided by a structure interposed between one arm of the water seal chamber and the collection chamber. The structure also prevents water siphoning into the collection chamber as pressure therein decreases, and prevents water entrained in air bubbles passing through the water seal during reinfusion from entering the collection chamber to contaminate the body fluids. Additional structure in one or more U-shaped water columns accommodates extreme pressure fluctuation without impairing the water seal, and permits fine control of relatively small suction ranges in normal operation. In a preferred embodiment, the system includes a spring-loaded transfer vessel which connects to the third port to provide a system wherein a single fluid connection adds or removes the transfer vessel. No additional valving, vacuum connections or other connections are required, and the drain line from the patient is not disturbed. Despite the significant changes thereby introduced in local pressure levels and total chamber volume, the desired suction level is maintained and collected fluids are removed from the chamber without interruption or system instability for disposal or reinfusion of the collected fluids.

It is accordingly an object of the invention to provide a reliable, easily used, inexpensive and disposable drainage device capable of simultaneous collection and autoinfusion of collected fluids, and which regulates subatmospheric suction pressure during both drainage and autoinfusion while minimizing introduction of ambient air into contact with the collected and reinfused fluids. Another object is to provide a versatile device which functions effectively intraoperatively as a suction-powered drainage device, and post operatively may be used to drain the pleural and mediastinal cavities without inducing excessive bleeding or fluid exudation and without damaging intrathoracic tissue.

BRIEF DESCRIPTION OF DRAWINGS

For a fuller understanding of the nature and objects of the invention, reference should be made to the following detailed description and the accompanying drawings, in which.

Throughout the description, like reference characters in respective drawn figures indicate corresponding parts.

DESCRIPTION OF ILLUSTRATED EMBODIMENTS

Figure 1:
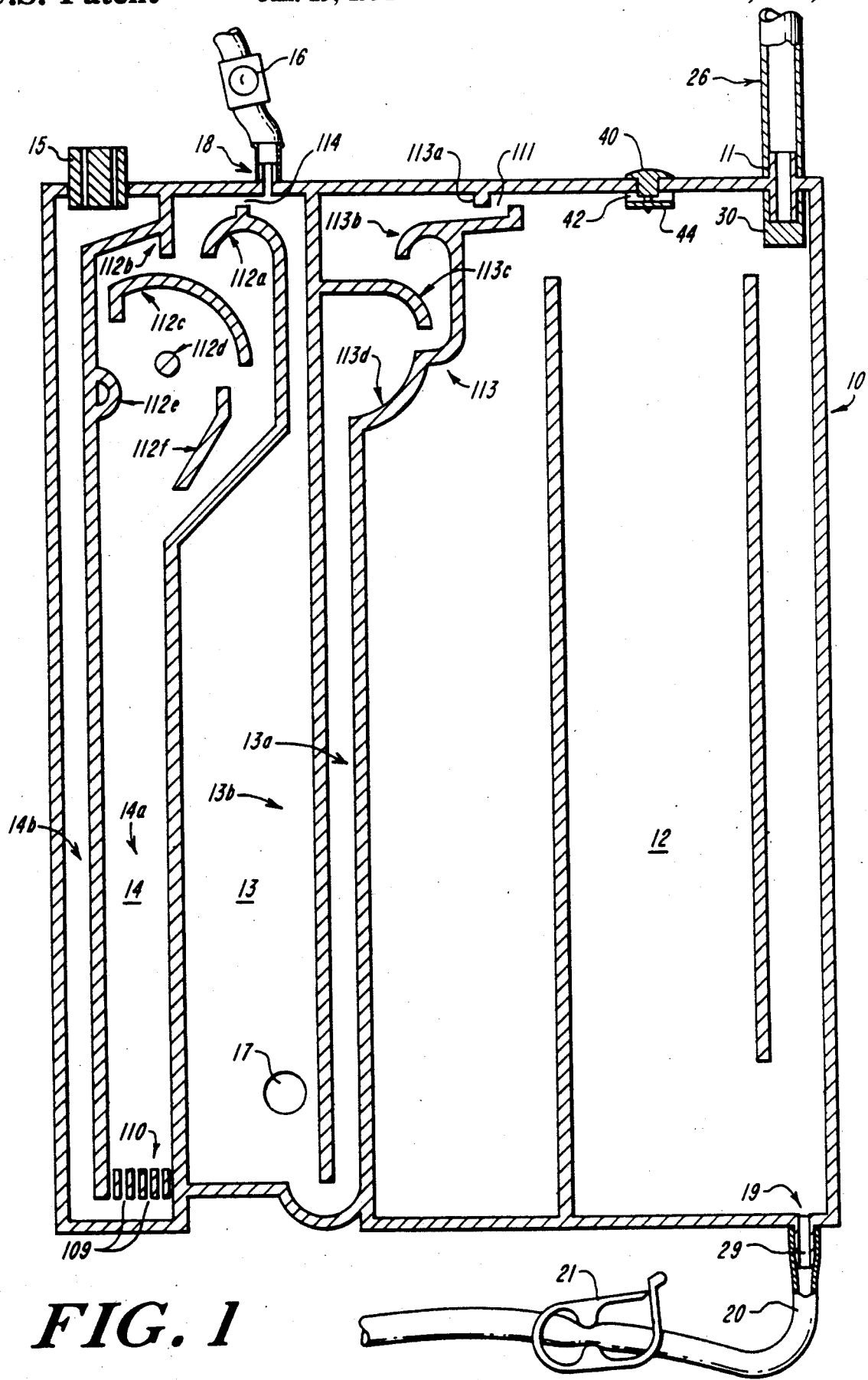
FIG. 1 is a sectional view of a basic drain device according to the invention.

Referring to FIG. 1, there is shown a chest drain device 10 which is preferably of unitary construction, fabricated by adhering together rigid molded parts of plastic, at least some of which, as described in further detail below, are transparent. The device generally comprises a collection chamber 12, a U-shaped water seal chamber 13, and a suction control or manometer chamber 14.

Blood and other fluids from a patient's body cavity enter drain device 10 through a tube 26 attached to inlet port 11, and are collected in collection chamber 12 after passing through a gross filter 30 which traps macroscopic debris such as blood clots, bone fragments, and the like entrained in the incoming fluid. Filter 30 preferably has an approximate pore size of 80-270 microns, suitable for filtration of such contaminants as bone and other tissue not suitable for blood transfusion. Collection chamber 12 is preferably provided with graduated markings (not shown) indicating the volume of fluid it contains.

Water seal chamber 13 provides a barrier to reflux of atmospheric air into a patient's pleural cavity. Water seal chamber 13 is a U-shaped chamber having two arms 13a and 13b, and preferably is provided with grommet 17 for filling with water via a syringe needle. Water seal chamber 13 preferably also has graduations to indicate fill level. Arm 13a of water seal chamber 13 is of smaller cross-sectional area than arm 13b, and communicates with collection chamber 12 via structure 113 and port 111. The upper end of arm 13b has a vacuum port 18 for connection to a source of vacuum. Water seal chamber 13 communicates with arm 14a of manometer chamber 14 through port 114. Arm 14b of manometer chamber 14 is vented to the atmosphere through vented plug 15, which is removable to allow filling of manometer chamber 14 with water. Manometer chamber 14 is preferably provided with graduated markings to indicate fill level. Arms 14a and 14b communicate via the narrow slits 109 in bubble indicator 110. The manometer chamber regulates vacuum by allowing air at atmospheric pressure to pass through the manometer water column and bubble indicator into the water seal chamber. The amount of water disposed in manometer chamber 14 serves to regulate the subatmospheric pressure in chambers 12 and 13 generated by the vacuum source attached to port 18. Specifically, when a vacuum source is connected to port 18, the subatmospheric pressure difference in the region of port 114 will be equal to the height in centimeters of the water column in arm 14a, under normal operating conditions.

Certain respiratory conditions can cause a sudden increase in pressure within the pleural cavity. For example, a cough or an air leak into the pleural cavity can produce a substantially higher pressure within the pleural cavity; such pressure must be relieved to permit normal respiratory function. Additionally, such a sudden increase in pressure is passed directly to the drain device by tube 26, and in a prior art device can force water out of the manometer chamber through vented plug 15. This is undesirable, since upon return to lower pressure in the pleural cavity, a substantially lower vacuum will be imposed on the cavity due to the lower remaining water volume in the manometer chamber. The device 10 avoids this problem in part by providing, in addition to the aforesaid Port and water column structure, a self-regulating, diaphragm-type, positive pressure release valve 16, located in the vacuum line attached to port 18.

Near the bottom section of collection chamber 12 is disposed a fluid removal port 19. The port includes a microemboli filter 24 preferably a 20-40 micron filter. Tubing 20 is attached to port 19 and is fitted with a conventional clamp 21 which controls the flow of fluid from chamber 12 into an infusion pump 28 (FIG. 2) or transfer/infusion vessel 50 (FIG. 3).

The embodiment of the invention of FIG. 1 also includes an optional valve 40 disposed in a valve housing 42 which communicates between chamber 12 and the ambient atmosphere. A bacterial filter 44 disposed in housing 42 assures that airborne microorganisms passing through valve 40 do not contaminate fluid contained in collection chamber 12. Valve 40 may comprise a manually operated valve, such as a pushbutton valve, which, when actuated, permits influx of air into chamber 12. Alternatively, valve 40 may comprise a check valve which opens in response to a preselected pressure differential on its opposite sides. The purpose of valve 40 is to provide alternative means for permitting influx of air into chamber 12 to relieve excessive subatmospheric pressure which may develop in chamber 12 during use of the drainage unit.

Figure 2:
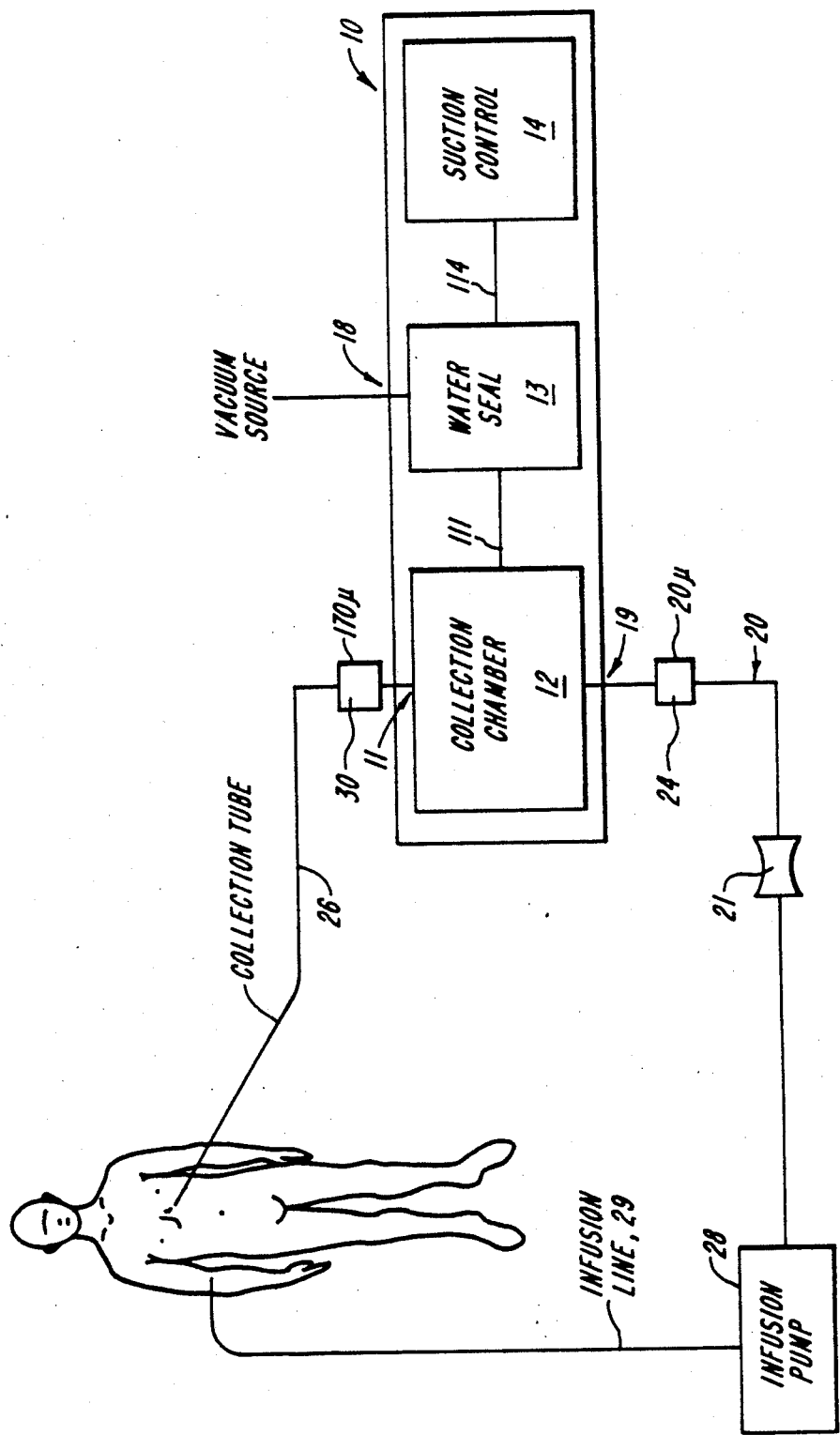
FIG. 2 is a schematic diagram showing an autotransfusion circuit according to the present invention.
Figure 3:
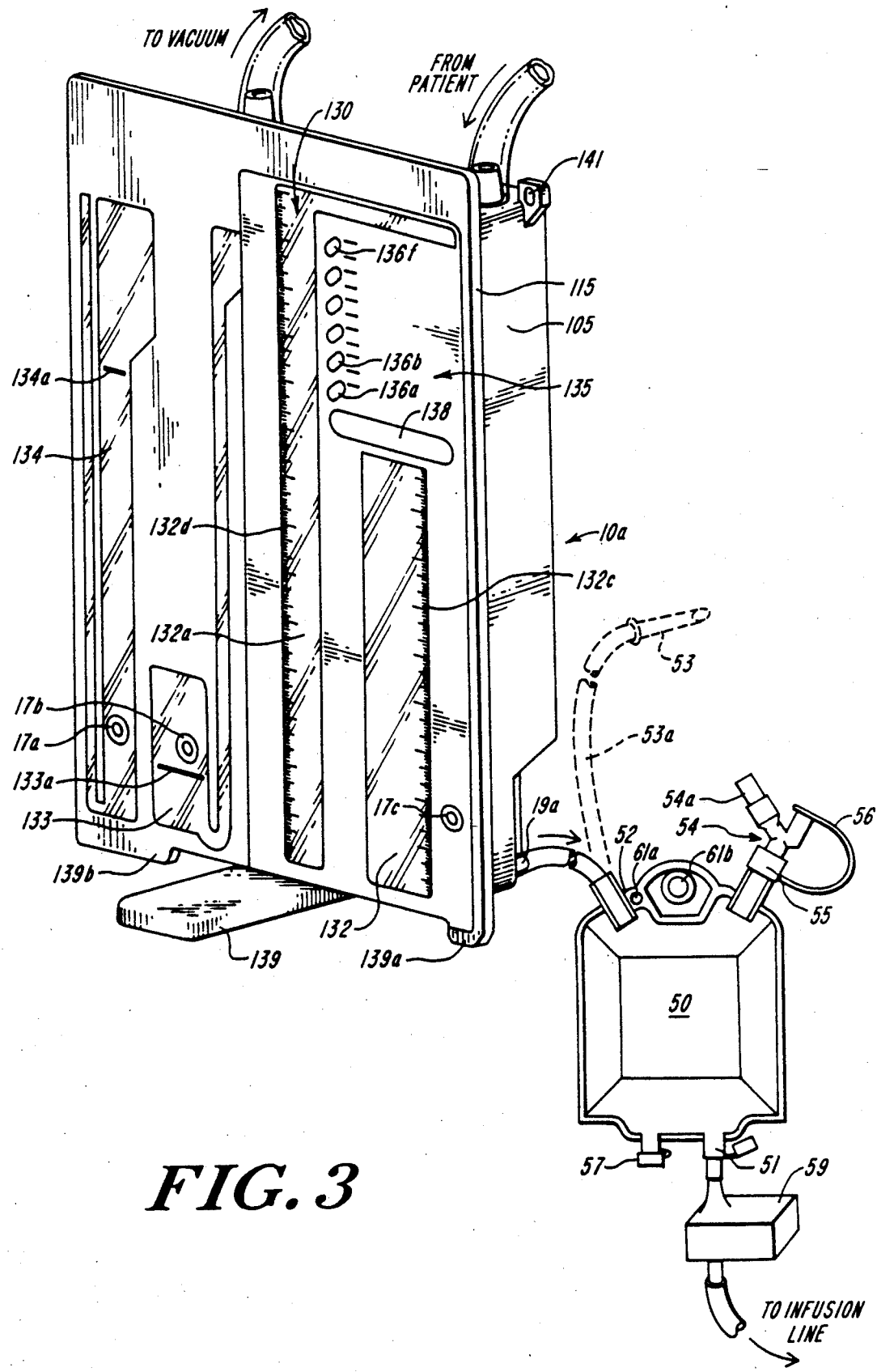
FIG. 3 is a front perspective view of a preferred system for implementing an autotransfusion circuit similar to that of FIG. 2.

Operation of the drain apparatus is best understood with reference to FIG. 2, a schematic of an autotransfusion circuit utilizing the invention. In use, water seal chamber 13 is filled with water to a preselected level, and manometer chamber 14 is filled with water to a level corresponding to a desired subatmospheric pressure. Thoracotomy tube 26 is connected to the patient and to port 11, and vacuum from a wall outlet or portable vacuum source is then applied to vacuum port 18. Vacuum modulated by air bled in through the manometer chamber is thereby applied to the collection chamber 12, and to the thoracotomy tube 26, and fluids such as blood are drawn into collection chamber 12. Such collection may be utilized in the emergency room, operating room, intensive care or other post operative settings.

When used intraoperatively, a conventional suction head (not shown) is sealed to the distal end of tube 26, and the surgeon periodically vacuums the patient's blood from the site of the incision. When used postoperatively, the thoracotomy tube 26 is implanted in a suitable location in the patient's body cavity, typically the pleural cavity, and fluid is withdrawn as it collects while a subatmospheric pressure compatible with normal breathing is maintained in the pleural cavity and in collection chamber 12.

Body fluids entering chamber 12 pass through filter 30 which traps particulate matter, assuring that the liquids collected in chamber 12 are free of macroscopic particles. Irregularities of the pressure in chamber 12 caused by coughing of the patient or "milking" of the thoracotomy tube 26 are accommodated automatically in the device by changes in water levels within the columns 13a, 13b of the water seal chamber 13. Fluctuations in the vacuum source attached to port 18 are modulated by the water in the manometers chamber 14 and positive pressure relief valve 16 which automatically permit influx or reflux of air as required to maintain internal subatmospheric pressure in the narrow range corresponding to the water columns.

In the system of FIG. 2, autotransfusion may be accomplished by opening clamp 21, thus permitting fluid to flow out through filter 24, port 19, along line 20, and into infusion pump 28, which returns fluids to the patient via infusion line 29.

Referring again to FIG. 1, the present invention allows for automatic regulation of negativity during autotransfusion by virtue of the cooperation of port 111 through which water seal chamber 13 communicates with collection chamber 12, and elements 113a through 113d of self-bailing structure 113. As fluid is autotransfused through port 19, subatmospheric pressure in chambers 12 and 13 are equalized through port 111 as air passes upwardly through chamber 13a, and water seal integrity is maintained by the structure 113, which prevents interchamber siphoning. Water rising as a column in chamber 13a and entrained as a mist in air bubbles passing through the column is confined in the structure 113 and returned to the water seal chamber. Similarly, elements 112a through 112f protect manometer integrity by preventing interchamber siphoning effects between the manometer and water seal chambers.

For intraoperative use, the water seal chamber may or may not be charged with water, at the option of the physician. Suction can be controlled via a wall outlet regulator, or via manometer chamber 14. In any case, use of the device in this manner provides more gentle suction levels than those attainable by prior art intraoperative drain systems.

Collected fluids can be reinfused on a continuous basis directly back into the patient through filter 24 and infusion pump 28, because the gentle and continuous suction automatically provided by drain 10 is compatible with the simultaneous outflow and inflow of blood from collection chamber 12.

In fact, because of this gentle suction regulation, collected blood may be withdrawn and reinfused in accordance with the invention without use of any electrical infusion pump or other major equipment. FIG. 3 shows such a non-mechanical autologous blood circuit.

A drain unit 10a substantially similar to the device of FIG. 1 has an outlet 19a at the base of its collection chamber 12 to which a transfer vessel 50 is connected to receive fluids collected in chamber 12. Transfer vessel 50 is a heavy plastic bag having an inlet 52, and an outlet 51, as well as a vent 54 having a microporous filter 55 and closure cap 56. Inlet 52 and outlet 51 are at opposed ends of the bag, with the top/bottom orientation defined by a hole 61b for hanging the bag in a vertical orientation. A pierceable sampling or medication injection port 57 is preferably also provided.

At the bottom of vessel 50 a separate microemboli filter 59 is interconnected between port 51 and an infusion line. Shown in phantom is a spike connector 53 and large bore PVC infusion tubing 53a which, in the preferred embodiment, are permanently connected to inlet 52 and adapted to couple with a mating diaphragm closure and spike-compatible connector extending from the outlet port 19a of the drain 10a. Before interconnection of the drain and transfer vessel, connector 53 is maintained in a sterile state in a sheath 54a formed on the vent manifold 54.

Transfer vessel 50 is adapted to generate its own suction, and preferably is a spring-loaded suction vessel, having an internal structure of the type, for example, which is illustrated in U.S. Pat. No. 4,429,693. For purposes of describing the conventional aspects of this vessel, the disclosure of that patent is hereby incorporated herein by reference. That patent shows a bag with an internal folding frame which is urged apart by a coil spring to exert a force on opposite sides of the bag, creating a strong and reasonably uniform suction. An embodiment of that patented spring-loaded suction vessel is presently marketed by the Johnson and Johnson Company as its "J-VAC" suction reservoir. In that device, a folding box-like internal frame placed about a coil spring is normally maintained in a substantially flat position by an internal latch. When the frame is slightly bent, the latch mechanism releases, and opposing walls of the frame are thereafter urged to unfold under the influence of the spring, creating an effective suction of 0.05 to 0.10 atmospheres.

For the practice of this invention, the precise suction level is not important, so long as it is sufficient to overcome the draw of collection chamber 12. An appropriate vessel is achieved by modifying the above-described commercially available suction vessel to further incorporate a capped and filtered vent, a capped outlet port vertically opposed to the vent, and preferably also a sampling port as shown in FIG. 3. In addition, the internal spring is suitably treated to meet USP blood compatability specifications for contacting blood which is to be reinfused, and blood-compatible polymers or coatings are used for the internal frame structure as well as the bag inner surface. For the particular transfer vessel described, the level of suction developed by the vessel, corresponding to a water column of twenty to fifty centimeters, is sufficiently stronger than the levels maintained in drain 10a, to readily draw out any fluids from the collection chamber 12 of the drain. The suction differential remains effective to drain the collector 10a when transfer vessel 50 is suspended at any height approximately level with or below the top of drain 10a.

Operation of the system for collecting fluids and reinfusing the collected fluids proceeds as follows. First, the drain 10a is set up by filling the manometer and water seal chambers to an appropriate level for achieving the desired suction. This level will depend on whether the device is used intraoperatively, or, if post operatively, on the nature of the thoracic drainage site and whether there is leakage into the thoracic cavity. Next, the vacuum source is connected, and then the drain line to the patient is connected. During this period, the outlet port is closed, or, if vessel 50 is connected, the port may be open so long as all vents and outlets of vessel 50 are closed and its spring mechanism is latched in the retracted position.

When a sufficient volume of blood for reinfusion has collected, vessel 50, if not already attached, is attached and its spring mechanism released. This draws the collected blood through port 19a from drain 10a into vessel 50.

Thereafter, the line from the drain outlet port is clamped, and vessel 50 is removed and its inlet is closed. The outlet of vessel 50 is then connected through a microemboli filter to an infusion line, and its contents are redelivered to the patient. This may be accomplished by placing a pressure cuff about vessel 50 for bolus delivery Alternatively, it may be accomplished by hanging the vessel at a suitable height above the patient, opening the filtered vent, and delivering the vessel contents by gravity infusion. For the bolus delivery, it is not necessary to disconnect the vessel from drain 10a, but only to clamp the PVC connecting line. However, it is generally intended that transfer vessel 50 not be re-latched or re-used, so it is preferable to simply disconnect the transfer vessel. Once disconnected, a second vessel 50 may be connected to receive a further unit of collected blood, and to similarly reinfuse the blood.

Returning to the drain 10a of FIG. 3, several features of the preferred embodiment are shown in the front perspective view, and are noted here before proceeding to a more detailed discussion of the interior shape of the preferred drain. Drain 10a is of a multichamber design wherein a unitary housing is formed of two portions. A molded rear or body portion 105 is preferably formed of a light-colored opaque plastic, and contains a number of baffles, walls and posts which extend to a common front plane and define the internal structure of chambers, ribs, ports and supporting elements much as previously discussed in relation to FIG. 1. Front panel 115 is formed of a transparent sheet of substantially uniform thickness. The body portion and the front panel are preferably assembled by linear vibration welding. For this purpose, slight protruding ridges may be formed in the inner face of the front panel to align with and seal to the linear wall portions of the body securely. The front panel, as illustrated, has a graphic mask 130 printed thereon defining a plurality of windows, status indicators and calibration or measuring indicators.

Among the "windows" defined by graphic mask 130 are a manometer window 134, a water seal window 133, and a collection chamber window 132, each of which is aligned over the corresponding chamber of the housing. Preferably fill lines 134a, 133a in the windows mark the appropriate water level to achieve a suitable suction level and water seal. In the illustrated embodiment, an additional window 132a is aligned over a second fluid collection column, which as discussed in greater detail below, is preferably at least partially isolated from the normal inlet-filtration-outlet circuit. Each of the windows preferably has a grommet port 17a, 17b, 17c which may be used, in the case of windows 133, 134 to fill or replenish the water column, and in the case of window 132 to sample the collected fluid.

Figure 4:
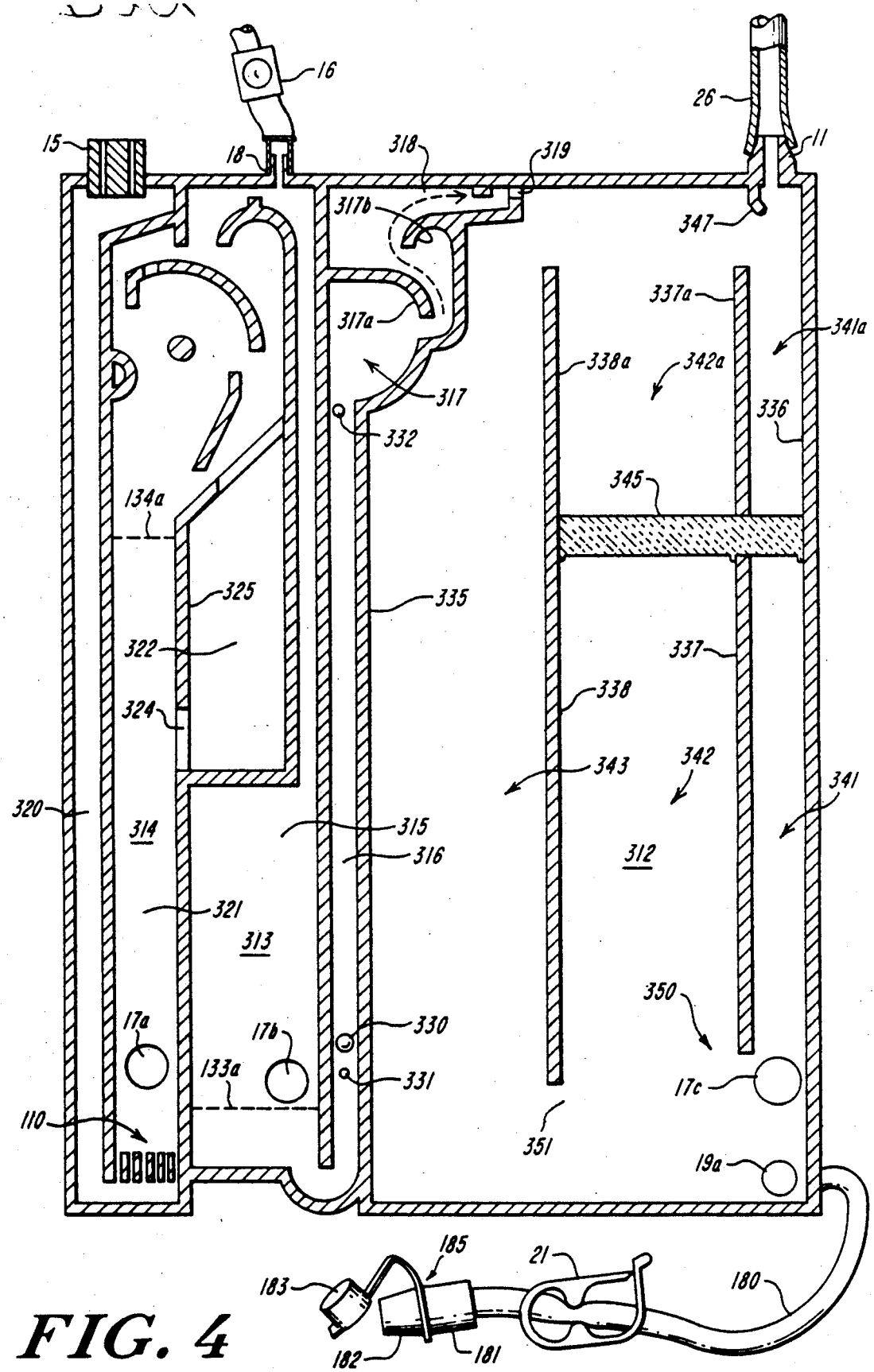
FIG. 4 is a sectional view of the drain device shown in the system of FIG. 3.

In addition to the aforesaid window structures, the graphic overlay 130 includes an opaque region 135 which, as described in greater detail in regard to FIG. 4, covers a portion of the drain having a large area gross blood filter, through which fluids drained from the patient fall to reach the collection chamber. Preferably, opaque region 135, or one of the columns or regions below it, contains a printed chart, e.g., a set of blank lines against a light matte ground, to write a schedule of fluid recovery, or a record of fluids transferred to a vessel 50 or to an infusion conduit. In opaque region 135 a series of small clear windows 136a–136f provide an indication of the level of fluid accumulated inside the drain over the gross filter, as described below, of which the general location and shape is indicated at 138. The level indicated by windows 136a-136f depends on the rate of blood collection, and on the volume of accumulated clots. When the level continues to rise, unfiltered blood overflows into the column of window 132b.

A pedestal 139 is rotatably attached to housing 105, and rotates out from the general plane of the drain device to provide, together with face plate protrusions 139a, 139b, a base and stabilizing feet to support the drain upright on a surface. An alternate means of support is to provide hooks from a pair of brackets 141 (of which one is visible in the figure) to hang the drain from a frame.

It will be observed that each of windows 133, 134 has a narrow and a wide portion. These portions lie over narrow and wide arms of the respective water columns. Another feature visible in FIG. 3 is that the housing of drain 10a is not of uniform front-to-back depth. For example, it will be seen that outlet 19a is located in a lower portion of the drain having a chamber thickness approximately half that of the upper portion. This geometry of differing chamber depths efficiently channels fluid to a lower collecting sump region. Other localized differences in a chamber depth or thickness, described in greater detail below, cooperate to provide a stable and highly uniform suction drain device.

FIG. 4 is a sectional view of the molded rear body portion 105 of drain 10a of FIG. 3, taken along a plane parallel to and slightly behind the front panel 115. To aid in visualizing the correspondence with features of FIG. 3, the fill lines 133a, 134a and grommets 17a, 17b, 17c are indicated on the Figure, although they are features of the panel 120. The pierceable sample/fill grommets 17 may alternatively be located in apertures in the rear wall of the body portion 105 in the positions indicated in FIG. 4. Certain details of FIG. 4 are also intended as schematic rather than as exact sections. For example, the float ball 330, described below, is simply shown in a perspective view for emphasis.

Drain 10a, like the basic embodiment of FIG. 1, includes an internal structure of walls which separate the interior into three chambers, namely a manometer chamber 314, a water seal chamber 313, and a fluids collection chamber 312, which are laid out in a series flow path, with the vacuum source connected to port 18 between chambers 314 and 313.

A principal feature of the illustrated device is that it achieves stable and safe suction levels despite changing conditions at the patient inlet port 11, and at the outlet/reinfusion port 19a. To this end, the walls defining the three chambers and the passages therebetween have the following properties.

Manometer chamber 314 includes a two arm U-shaped water column wherein a first arm 320 which is open to the atmosphere via plug 15 has a cross-sectional area substantially below (e.g., less than one tenth) that of the second arm 321 which communicates with vacuum port 18. Such an arrangement limits the amount of water which is drawn from column 320 into column 321 when suction starts, so that the resting height of the water column 321 accurately reflects the intended suction level. It further limits the amount of water which can be blown from column 321 into column 320 in the event of a pressure surge in the interior of the drain, so that short time pressure fluctuations are modulated by the expenditure of energy in pushing water along the column, and abrupt water losses which might disable the device do not occur. A third sub-chamber 322 communicates with arm 321 via lateral opening 324 in a divider wall 325. This sub-chamber effectively doubles the fluid-holding capacity of the manometer chamber, yet is spaced out of the air flow path between the bubble-former 110 and the vacuum port 18, so that water in the sub-chamber is shielded from the evaporative losses due to airflow through chamber 314 which would otherwise regularly degrade the accuracy of the suction setting. This multi-subchamber arrangement stabilizes the suction level over the long term, as well as providing a larger buffer volume to prevent fluid loss from pressure back-surges.

As in the embodiment of FIG. 1, a plurality of curved baffles (not numbered) in the upper portion of the manometer chamber return condensate to the water column.

The volumes of water required to achieve a given suction level in a prototype embodiment are set forth in the following table of manometer fill volumes. It will be seen that the higher suction levels are achieved with a more than proportionately larger volume of water.

TABLE I

| Desired Suction Pressure | Approximate cc Volume |
| --- | --- |
| −20 cm H$_2$O | 320 cc |
| −15 | 180 cc |
| −10 | 80 cc |
| −5 | 38 cc |

The water seal chamber 313 similarly includes a pair of arms of imbalanced cross-sectional area, 315, 316 with the smaller-section arm 316 communicating via a reflux structure 317, a tortuous path 318 and a baffled port 319 with the blood collection chamber 312. As with the arms of the manometer chamber, the smaller arm 316 preferably has a cross-sectional area which is ten percent or less times that of the larger arm 315. At the top of arm 316, however, the portion of the arm containing the reflux structure is enlarged so that, in the event an extreme underpressure condition should occur in the collection chamber 312, the fluid from arm 315 may be accommodated within arm 316 and will not be drawn through port 319 into the collection chamber.

In the event that a rush of water is sucked up arm 316 toward port 319, a plurality of turning baffles 317a, 317b placed in the path serve to catch the rising column and deflect back he moving water, thus using the moving fluid's own energy to slow the pressure-induced surge, and thereby accommodating extreme pressure surges in the collection chamber without disabling the drain device. Such deflection keeps the water seal intact under broader conditions, and the narrow column 316 is of a dimension such that bubbles which have entered from column 315 may be drawn back down the column, as in a capillary column. The arrangement of baffle structure, tortuous path and port 317, 318, 319 is such that fluid from the water seal does not generally reach the collection chamber, and air which may be drawn through the seal during a short violent spasm is re-entrained in the normal evacuative flow toward suction port 18 when the pressure levels return to normal. This construction is generally adequate to prevent contaminants from entering the collected blood. Moreover, the invention further contemplates the provision of a filtered pressure relief valve (not illustrated) as in valve 40 of FIG. 1.

A float ball 330 rides in column 316 between two permanent posts 331, 332 formed in body portion 105, so that the level of the float provides an indication of an anomalous underpressure in chamber 312, visible through window 133 (FIG. 3). When the ball indicates an anomalously high suction in the collection chamber, the valve 40 may be actuated, or the suction will be automatically lowered by the passage of air from columns 315, 316.

The third major sub-chamber, the collection chamber portion 312, of this embodiment of a drain device is defined by the outer contours of the molded body portion 105 as well as by an internal wall 335 which extends for the entire height of the drainage device. Wall 335 separates the collection chamber 312 from water seal 313, so that the two chambers communicate only at port 319 as described above. Port 319 has a cross-sectional area of approximately one-half square centimeter in the prototype device. The total volume enclosed by the body 105, 115 of that prototype is approximately three liters, comparable to the volume of the pleural chamber. Of this amount, collection chamber 312 constitutes two or more liters. While the patient connection at port 11 is a large diameter thoracotomy tube which can transmit fairly abrupt pressure impulses to chamber 312, port 319 limits the attainable flow rates and thus modulates pressure impulses which are initiated on either side of the port.

Between the chamber-defining wall 335 and the outer side wall 336, one or more partial or complete intermediate walls 337, 338, which are integrally formed with the housing body portion 105, separate chamber 312 into sub-chambers 341, 342 and 343 as discussed below. The intermediate walls 337, 338 also support a large-area fall-through filtration element 345 below inlet 11, and extend to one or more upper wall portions 337a, 338a which provide an impoundment for fluids which have not passed through the filtration element 345.

As shown, a fluid deflector 347 spaced below the fluids inlet 11 channels the incoming fluid so that it falls straight downward into the upper portion 341a of the extreme right sub-chamber 341, onto filter 345. Filtered blood then seeps through. This fall-through filter arrangement minimizes mechanical trauma to the blood. Filtration element 345 is a large area gross filter, such as a fabric or an open-pore sponge filter, which is effective to remove clots and gross particles from the incoming fluids. It may be treated with an anticoagulating agent to pre-process the fluids passing through it. The filtered fluids then pass to the lower portion of chamber 341 where the back portion of the body angles forwardly to form a portion of lesser front-to-back depth constituting a collection sump at outlet port 19a.

When the drain receives an unusually large flow of fluids or the filter 345 becomes blocked with clots, the incoming fluids are impounded by wall 337a and eventually overflow into the space 342a between upper walls 337a and 338a. The overflow fluids contact a fresh area of the filter 345, through which they pass to chamber 342. Lower chamber 342 also communicates directly with sump region 350 and thus with the outlet port 319a.

Further, if the rate of fluid intake or amount of clots causes the impounded fluids in the space 342a to overflow, they pass over the top of wall 338a. In that event, the fluids pass without being filtered into an overflow collection sub-chamber 343 of chamber 312. The level in the filter impoundment space 342a is visible through the filter/flow status windows 136a–136f (FIG. 3), so that an excessive bleeding rate or clotting condition is easily detected by hospital personnel. The provision of an open, fall-through filter in this manner prevents back-up of fluids in the thoracotomy inlet tube from the patient, a common cause of tamponade, while still providing prefiltration of scavenged blood. This is a distinct improvement over a closed sock-type filter as used in prior art devices.

As shown in the Figure, a passage 351 is provided between chamber 343 and the sump area 350. In alternative embodiments, this passage may be omitted so that the overflow fluid is fully isolated. The windows 132, 132b (FIG. 3) may provide separate graduated fluid volume scales 132c, 132d, with the graduations on scale 132c representing the volume in chambers 341 and 342, and those of scale 132d representing the unfiltered volume in chamber 343.

Figure 13:
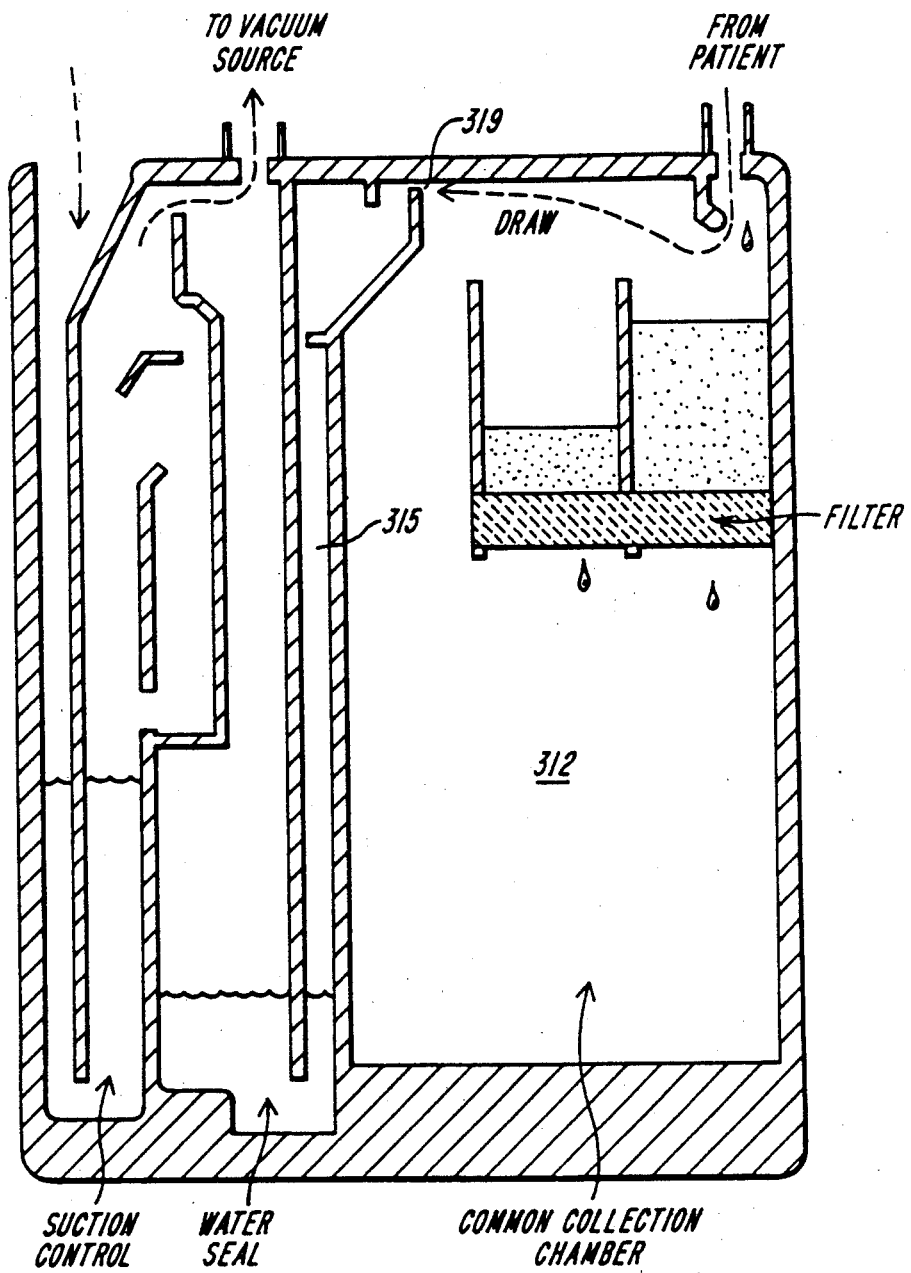
FIG. 13 illustrates interior operating characteristics of the drain device of FIGS. 3-9.

It will be seen that the structure of walls, baffles and ports just described results in the provision of a suction drain vessel wherein bidirectional pressure fluctuations are substantially compensated, and abrupt pressure impulses are modulated to more gradual perturbations that do not interrupt the functioning of the device. A further feature of note is that normal suction draws are established such that the diffusion path to the collected blood is relatively isolated. FIG. 13 illustrates the normal directions of flow in the device of FIG. 4.

From inlet 11, airflow, if any, is normally along the top of chamber 312, toward port 319. Blood entering at port 11 thus has a relatively low probability of encountering airborne contaminants, and it falls downward into chamber 341 or 342, where it is isolated from moving air. Thus, in the rare event air from water seal column 315 is drawn past port 319, it is unlikely to result in significant contamination, and the collected blood will be safe for reinfusion for at least the duration of a surgical operation or procedure.

FIG. 4 also illustrates a preferred outlet structure 185 attached to reinfusion/outlet port 19a. Port 19a is located at the lowest point of the drain, and has an large bore PVC infusion tube 180 attached thereto, with a pinch clamp 21. At the end of tube 180, an IV spike port 181 having a diaphragm closure 182 and reclosable cap 183 allows the sterile connection to transfer vessel 50 or to a conventional infusion pump or line. The position of port 19a assures that collected blood is entirely drawn out, thus minimizing the risk of contamination of the collected fluid. The large bore IV tubing allows fast delivery of the collected fluid.

Figure 5:
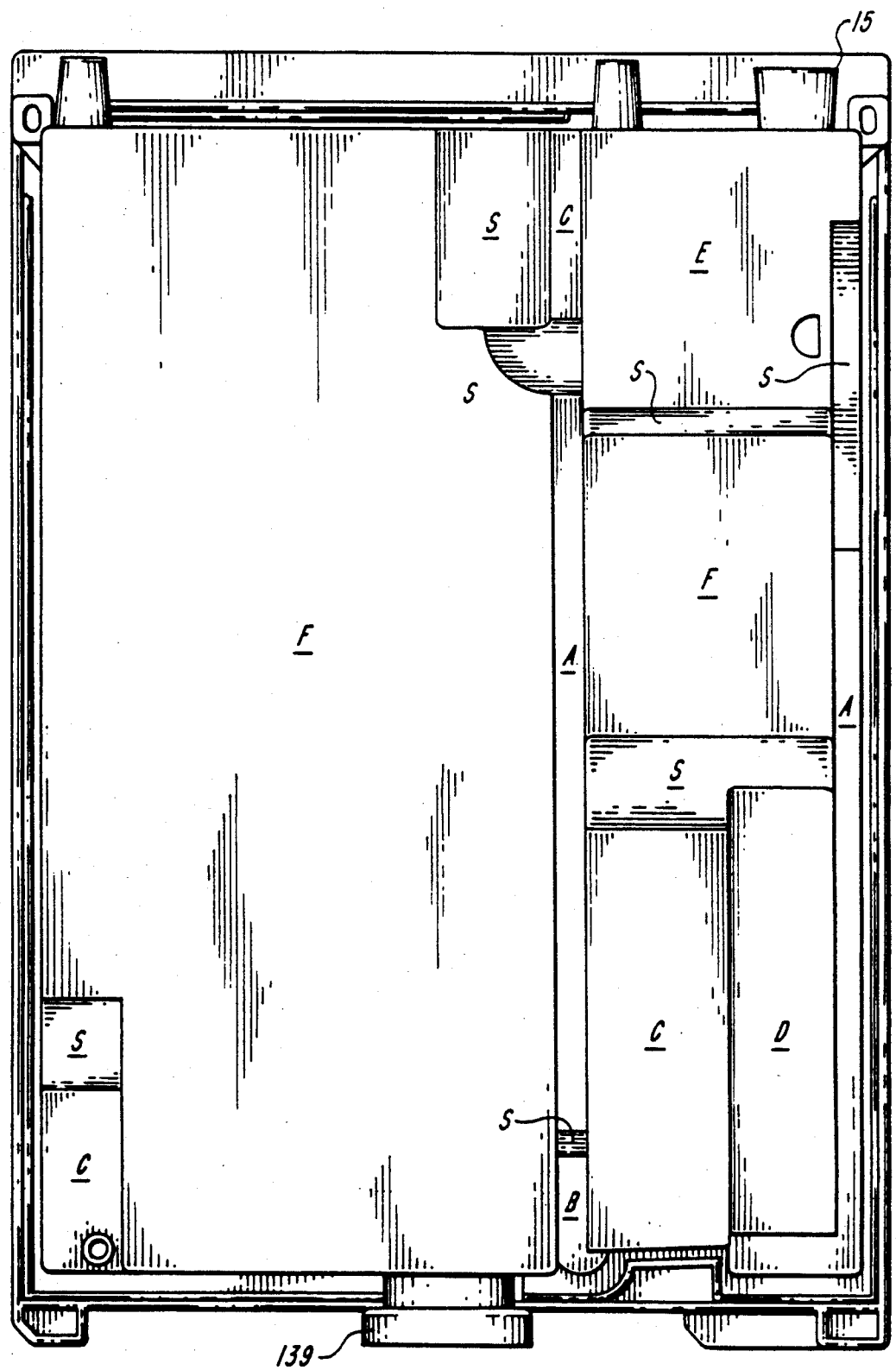
FIG. 5 is a back view of the drain device shown in the system of FIG. 3.
Figure 6:
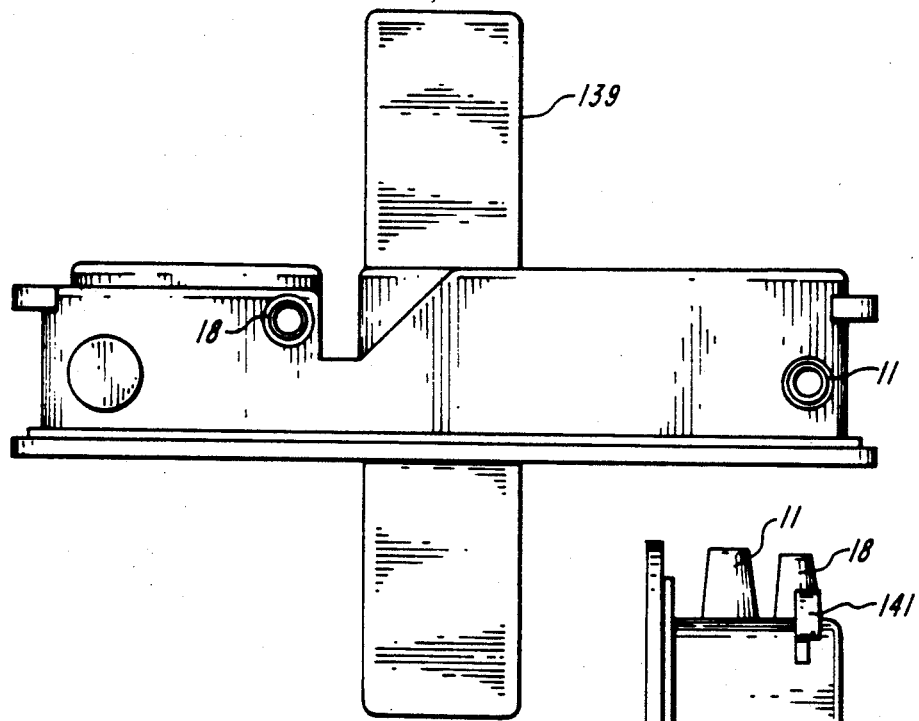
FIG. 6 is a top view of the prototype drain device of FIGS. 3 and 5.
Figure 7:
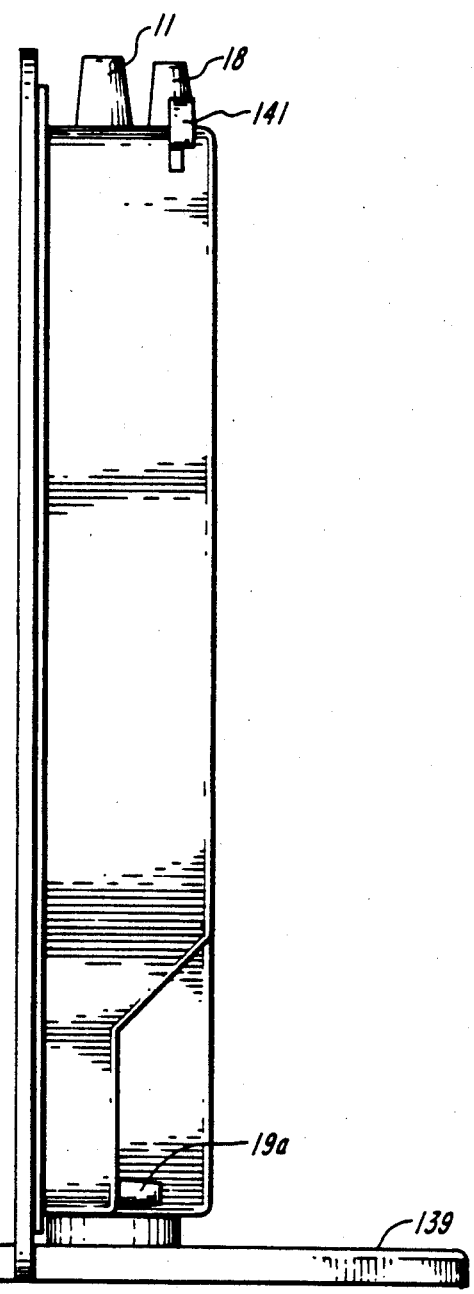
FIG. 7 is a side view from the collection chamber side of that drain device.

FIG. 5 shows a back view of the molded body portion 105 of the two-piece housing of drain 10a. The rear wall portion 105 consists of an arrangement of substantially rectangular panels each of which defines all or a portion of the rear wall of one or more of the sub-chambers or water columns described in respect of FIG. 4. In this preferred embodiment, each of the substantially rectangular panels lies parallel to the front panel at a depth "d" which is one of a few discrete values. In the illustrated prototype embodiment, which has an overall thickness or chamber depth of approximately two inches, the depth values A, B, C, D, E or F are given in the following table.

TABLE II

| Depth "d" | Inches |
|---|---|
| A | ¼ |
| B | ½ |

TABLE II-continued

| Depth "d" | Inches |
| --- | --- |
| C | 1 |
| D | 1½ |
| E | 1¾ |
| F | 2 |

The regions marked "S" in FIG. 5 are slanted back wall portions which lead from one chamber depth to a different chamber depth.

This back wall structure has been found to provide a particularly advantageous set of pressure response characteristics for the columns and chambers defined thereby, as well as providing a distinctive and visually pleasing outer form quite different from the awkward box-like appearance of conventional chest drain devices.

Figure 8:
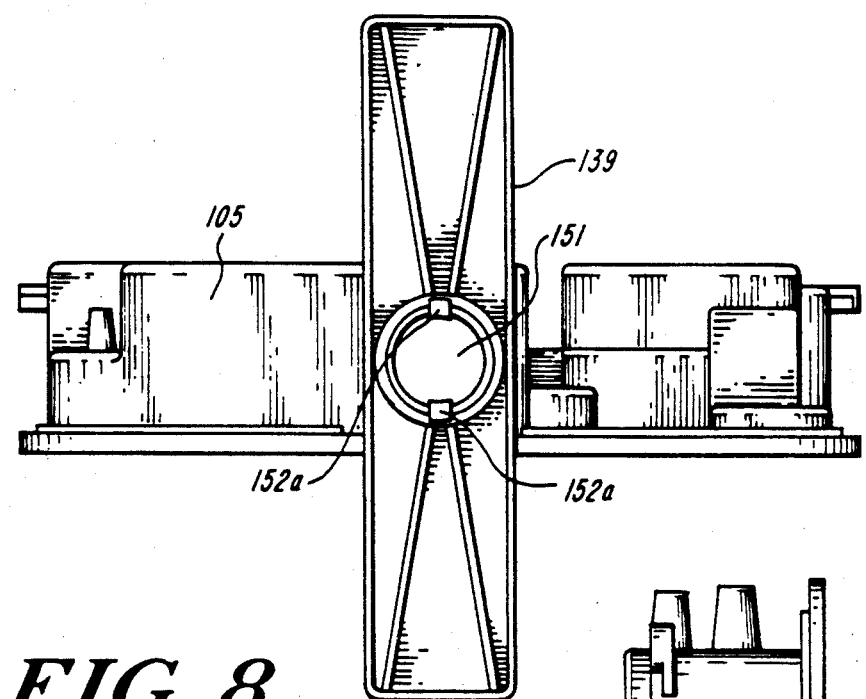
FIG. 8 is a bottom view of that drain device.
Figure 9:
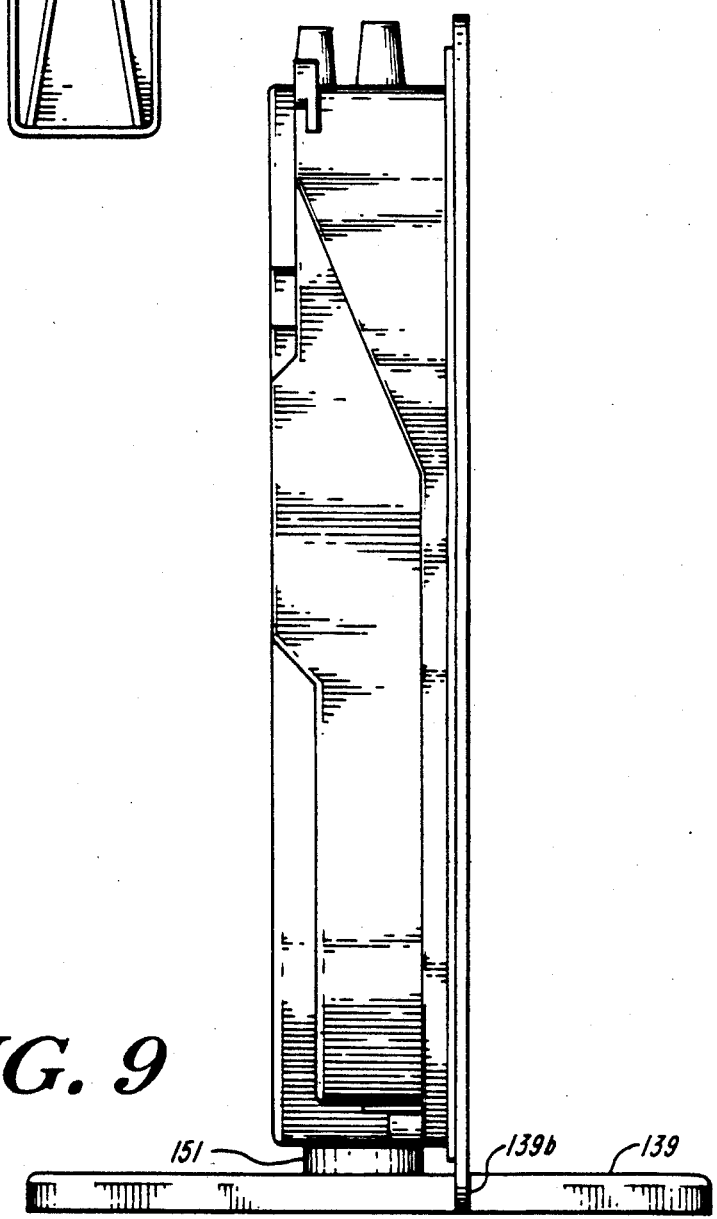
FIG. 9 is a side view from the manometer chamber side of that drain device.

FIGS. 6-9 show additional external views of the presently preferred prototype drainage device, illustrating in detail the contours and locations of the various wall, port, support and other features formed in the molded housing in this preferred construction. Among other details, these drawings show clearly the relatively large patient inlet port 11 (FIGS. 6, 7) which connects to and is preferably pre-packaged with, a large-diameter flexible latex thoracotomy tube. The transfer/infusion port 19a (FIGS. 7, 8), by contrast, connects to a smaller blood-compatible PVC tube. Preferably, the drain device is pre-packaged with a short, e.g., half-meter length of such tubing mounted on the port 19a, and having a sealed diaphragm-type spike port at its end. FIGS. 8, 9 show a cylindrical shaft 151 with stops 152a formed on the housing 105. Pedestal 139 is rotatably secured on shaft 151 by the stops, which also serve as detents to lock the pedestal perpendicular to the plane of the device when the pedestal is rotated.

Figure 10:
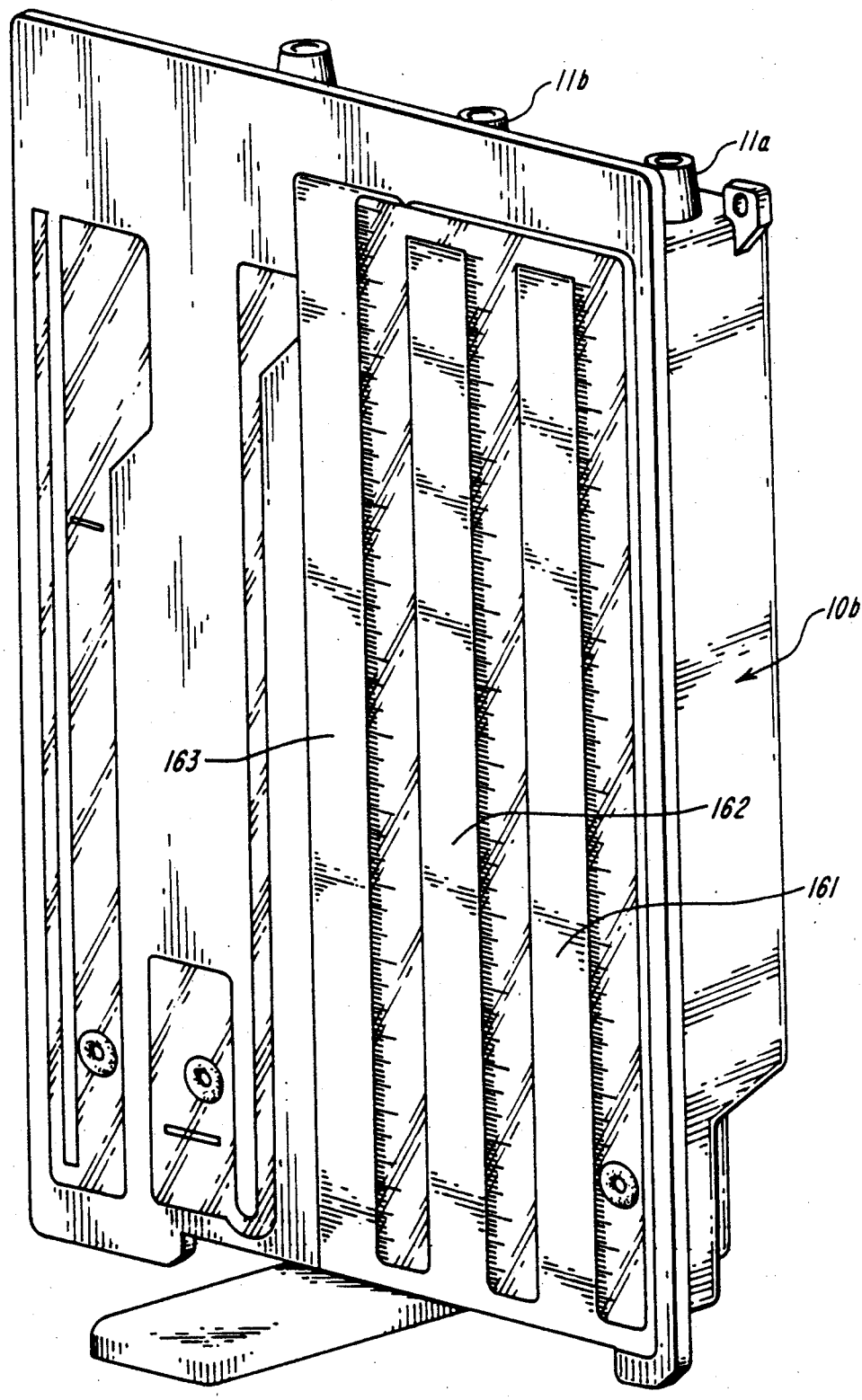
FIGS. 10, 10A, 11 and 12 are front perspective views of four different drain devices embodying different aspects of the invention.
Figure 11:
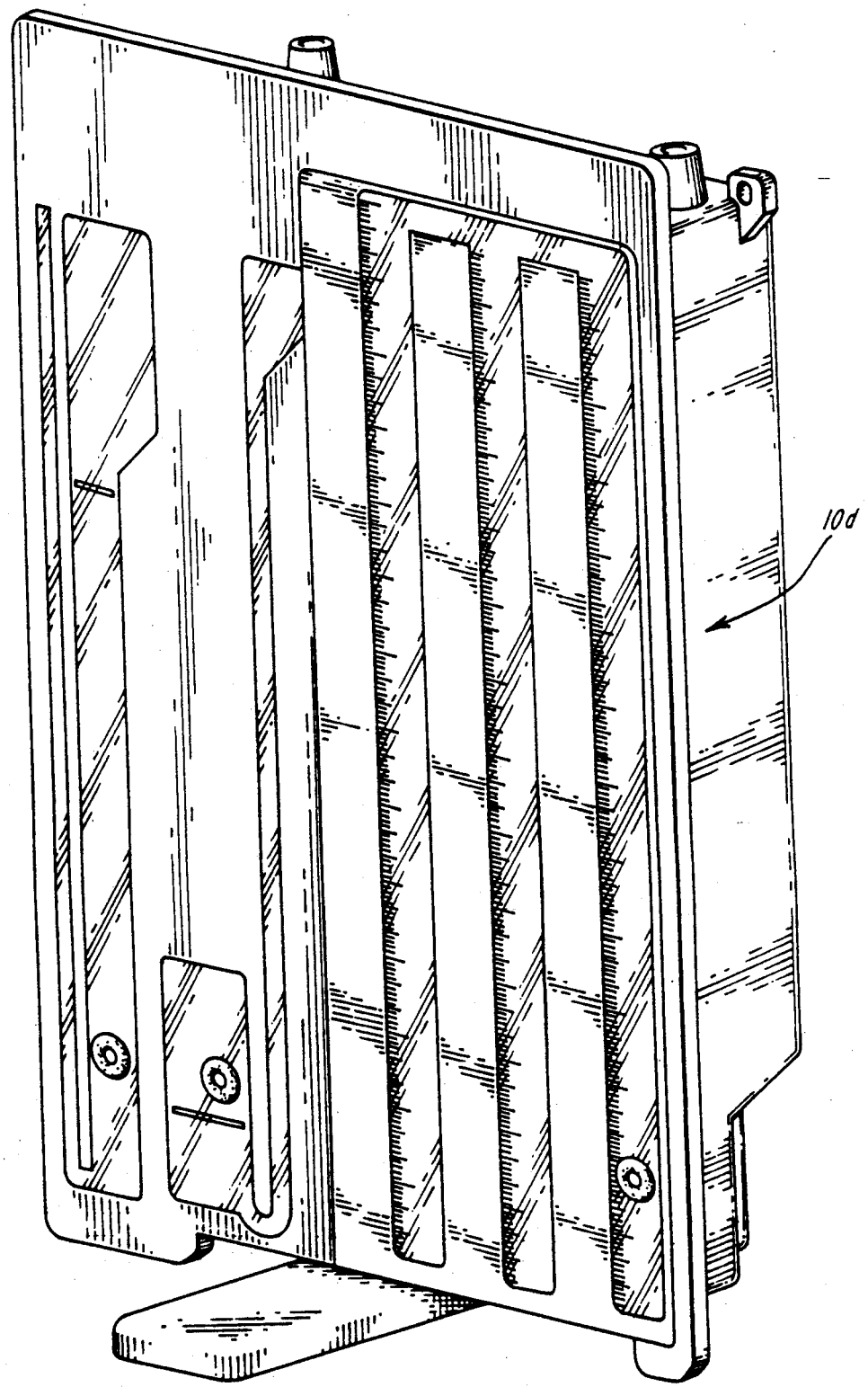
Figure 12:
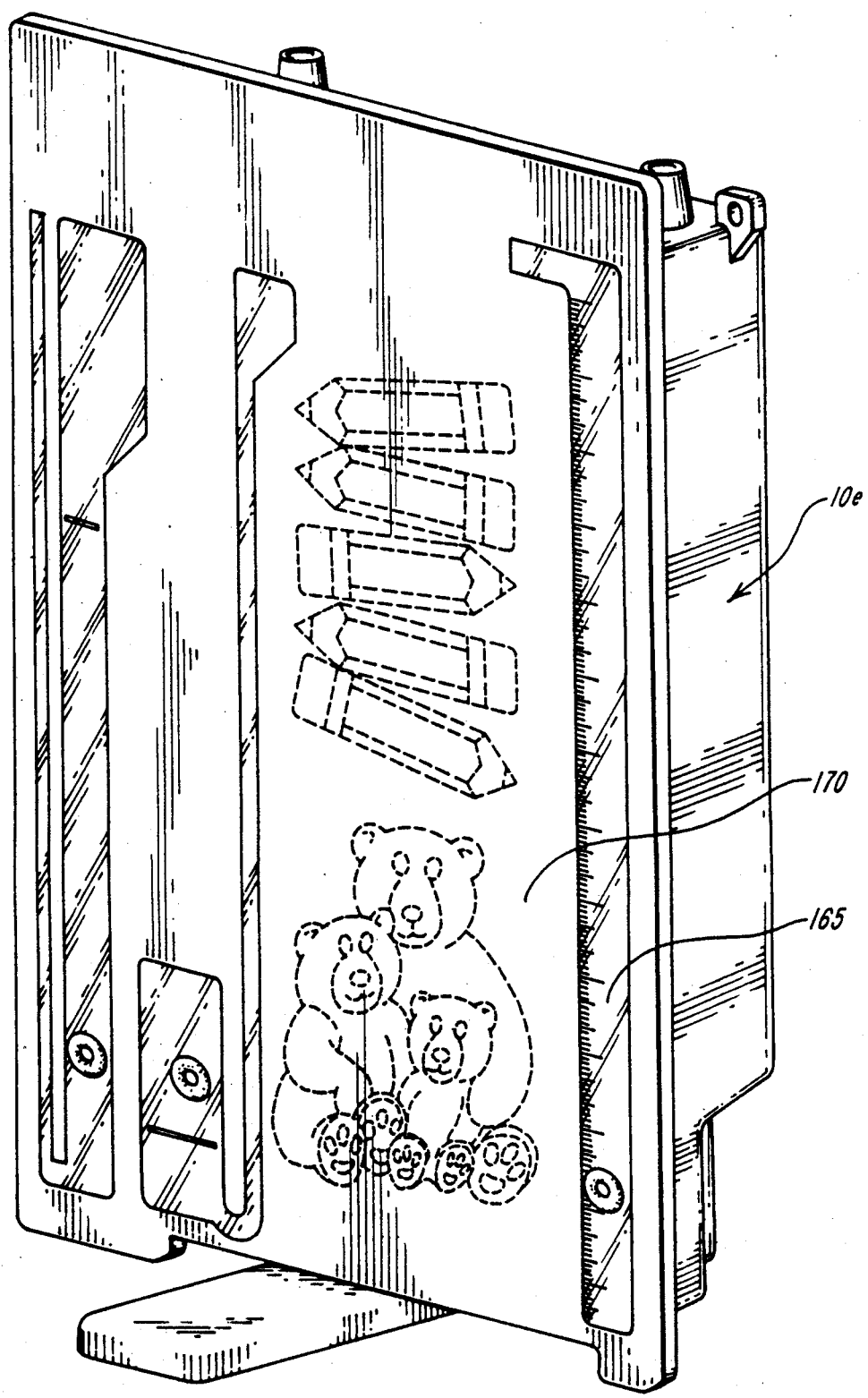

One or more of the foregoing features of the drain device are also advantageously incorporated into different drain devices illustrated in FIGS. 10-12.

FIG. 10 shows another drain device 10b which is specially adapted to collect fluids from several sites via plural patient fluid inlet ports 11a, 11b. In this device, the manometer and water seal chamber structure are substantially identical to those illustrated in FIGS. 3-5, but the inlet ports 11a, 11b lead to different collection chambers so that the volume of fluid collected from each site may be separately ascertained from the graduated windows 161, 162, 163. In this embodiment no outlet port or gross filter is provided, and the drain serves to collect fluid and monitor collected fluid levels. It is thus not intended for fluid reinfusion. A principal collection chamber under inlet 11a has two columns located behind windows 161 and 162, respectively. A continuous wall similar to wall 337 of FIG. 4, but extending entirely to the bottom, separates the two columns and assures that first one column fills and then overflows to fill the other column. Behind window 163 a single isolated secondary collection column receives fluids only from inlet 11b, and separately indicates their volume.

Figure 10A:
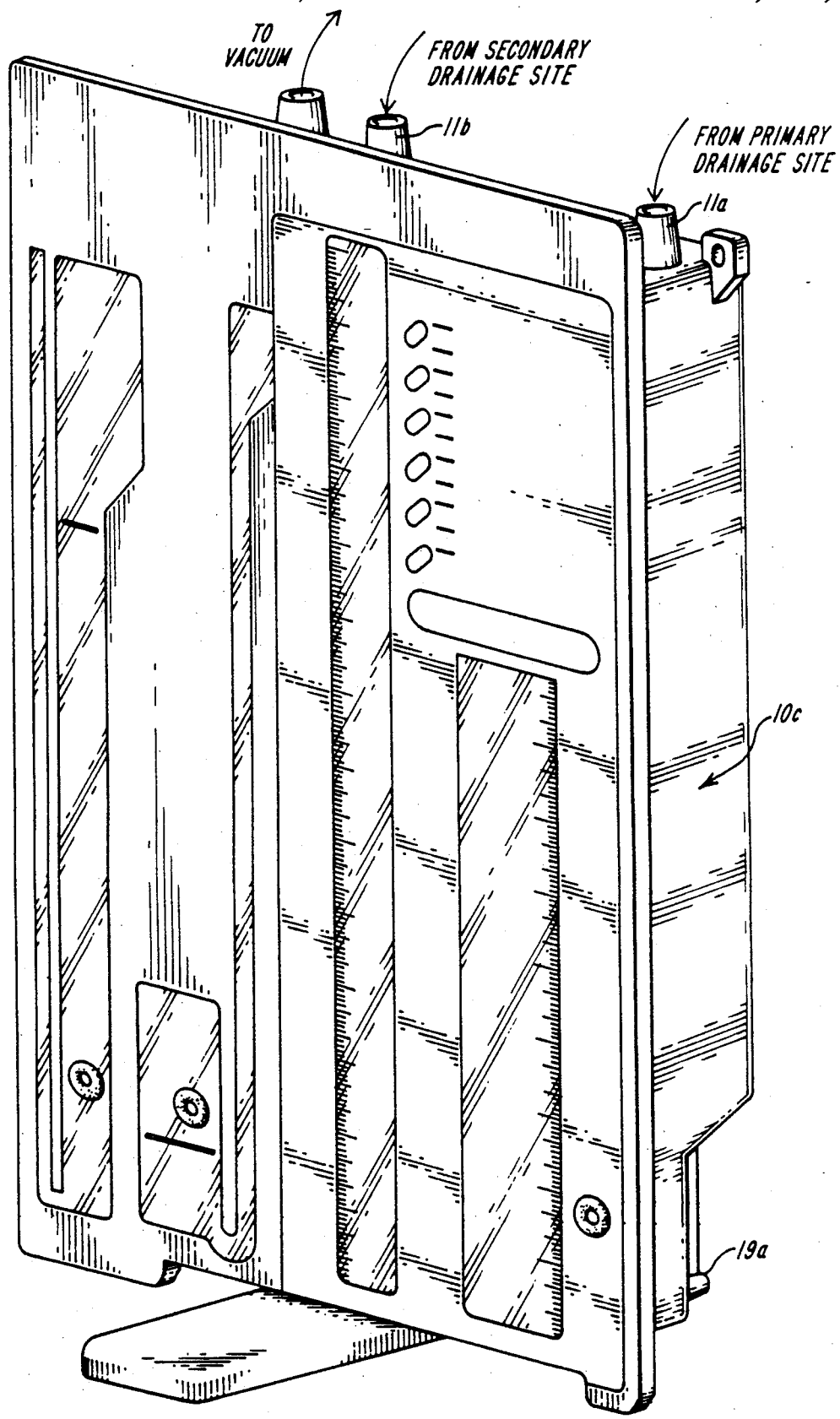

FIG. 10A shows another drain embodiment 10c having two patient inlets 11b, 11a. In this embodiment, a filter and outlet port 19a are provided for prefiltering and reinfusion of the fluid collected via inlet 11a, which is the primary inlet for mediastinal fluid drainage Secondary inlet 11b provides unfiltered collection from a secondary site, such as one at the apex of the lung, into a preferably isolated separate graduated column.

FIG. 11 shows another drain unit 10d with a single inlet and no outlet. In this embodiment, first and second inner walls define successive overflow paths to fill first one column, then the second, then the third. Again no gross filter or fluid outlet is provided.

FIG. 12 shows another drain unit 10d according to the invention. This drain is a pediatric drain, and employs the same water column structure as the preceding devices. It includes neither a gross filter nor an outlet port. The inner walls corresponding to walls 337, 338, 335 of FIG. 4 are modified to define a single collection column located behind window 165, and the column is dimensioned such that its full height corresponds to a fluids volume of only approximately two to five hundred cubic centimeters. A broad portion 170 of the panel covering the dead space between the collection column and the water seal has a bright engaging picture, represented in phantom, thereon.

Thus, the drain device described in relation to FIGS. 3-9 is adapted, with minor changes of straight interior wall portions and different printing on the front face, to provide a stable and sterile suction drainage device for a variety of drain applications and autologous blood circuits.

It will be appreciated that numerous of the features shown can be used independently of others and in a variety of drain device forms and structures. It will thus be seen that a chest drain device according to the invention efficiently attains the objects set forth above as well as those made apparent from the preceding description. Since changes may be made in the illustrated device without departing from the scope of the invention, all matter contained in the above description or shown in the accompanying drawings is to be interpreted as illustrative and not in a limiting sense.

Having described the invention, what is claimed as new and secured by letters patent is:

1. A drain device for draining blood and fluids from the thoracic cavity of a patient, such device comprising a multichamber vessel of a total volume comparable to the pleural volume of a patient, said device including a manometer for establishing a predetermined suction level, and wherein the multichamber vessel includes
   (i) a collection chamber having an inlet port for connection to the patient, an outlet, and a pooling region, and
   (ii) a water seal U-column having an inlet port connected to said collection chamber outlet, and an outlet at the manometer to normally sustain is predetermined suctional draw in said collection chamber toward said manometer, and wherein said water seal inlet port is spaced from said water seal column along a path extending within said multichamber vessel and including a plurality of baffles spaced along a vertical path over said water seal column for reversing the direction of water rising in said column, and has a dimension sufficiently small to modulate abrupt pressure variations in said collection chamber caused by patient spasms, thereby effectively preventing back flow from said water seal to said collection chamber, whereby blood collected in said collection chamber is suitable for reinfusion in the patient.

2. A drain device according to claim 1, further having at least one additional collection chamber and an additional inlet port separately communicating with said additional collection chamber, said water seal and manometer chambers being in suction communication with said at least one additional chamber whereby fluids from plural patient sites may be simultaneously and separately collected and monitored by said device.

3. A collection system for controlled aspiration and collection of body vital fluids, such system comprising
a first vessel for aspirating and collecting said vital fluid and means included in said first vessel for transferring collected vital fluid from said first vessel,
wherein the first vessel comprises
(i) a chamber having at least first, second and third openings therein adapted for communication with the atmosphere, with a hospital vacuum source, and with a vital fluid collection tube, respectively, said chamber being subdivided to provide a buffered volume of a least first, second and third successive intercommunicating sub-chambers having said respective first, second and third openings therein,
(ii) first and second water columns included in said first and second sub-chambers to define during normal operation first and second pressure differentials for establishing unidirectional flow from said first and third openings to said second opening while maintaining a desired subatmospheric pressure range in said third sub-chamber,
(iii) energy absorbing means for absorbing energy of pressure variations of said third sub-chamber, said energy absorbing mean cooperating with said water columns to effectively maintain said desired first subatmospheric pressure range,
said third sub-chamber including plural collection bins and a filter selectively positioned in said third sub-chamber below said third opening in a fall-through filtration path to at least one said bin, said filter being supported by a divider structure defining an unfiltered overflow path to a said bin, said third sub-chamber also having a fourth opening at a lower portion thereof, and
a flow means for fluid interconnection of said fourth opening with a second vessel, and wherein said first and second water columns with said energy absorbing means are effective to maintain said pressure range and continue to draw vital fluid through the vital fluid connection tube even when suction is applied via the flow means for drawing off collected vital fluid from said vessel.

4. A system according to claim 3, wherein said energy absorbing means includes means defining a tortuous path in series with a said water column for expending kinetic energy of said water column induced by pressure variations in said third sub-chamber.

5. A system according to claim 4, wherein said tortuous path includes a baffle for reversing the direction of motion of fluid in said water column.

6. A system according to claim 3, wherein said energy absorbing means comprises selectively sized apertures located between said first, second and third sub-chambers for damping propagation between said sub-chambers of abrupt pressure variations introduced in said third sub-chamber.

7. A system according to claim 3, wherein aid flow means includes means for removably attaching a spring-loaded second vessel to said fourth opening for generating said suction by mechanically expanding said second vessel.

8. A system according to claim 7, wherein said second vessel attaches to said first vessel via an inlet port located at an end of the second vessel, and said second vessel further comprises an outlet port located at a vessel end, a microporous vent located at a position opposed to said outlet port, and a closable vent for normally maintaining said vessel closed to develop suction, said vent being openable to allow venting of the second vessel when detached from the first vessel so that fluid collected in the second vessel may be infused to a patient without transfer to another container or additional processing.

9. A system according to claim 1, further including a microemboli filter for removing clots.

10. A vessel for aspirating and collecting vital fluid, such vessel comprising
(i) walls formed of polymeric material and defining an interior chamber having at least first, second and third openings therein adapted for communication with the atmosphere, with a suction source, and with a vital fluid collection tube, respectively, said interior chamber being subdivided to provide a buffered volume of at least first, second and third successive intercommunicating sub-chambers having said respective first, second and third openings therein,
(ii) first and second water columns included in said first and second sub-chambers for providing during normal operation first and second pressure differentials in said interior chamber effective to establish a unidirectional draw at each said first and third openings toward said second opening while correcting changes in pressure to maintain a desired subatmospheric pressure range in said third sub-chamber,
(iii) energy absorbing means for absorbing energy of abrupt pressure variations of said third sub-chamber, and including,
(a) a vertically disposed tortuous path including baffle elements located above a water column and positioned to reverse the direction of motion of the water column when the column moves due to variation in pressure, and
(b) an aperture sized for regulating abrupt pressure changes between said second and third chambers,
said energy absorbing means being operative with said water columns to effectively maintain uniform said desired subatmospheric pressure range, said third sub-chamber also having a fourth opening at a lower portion thereof and a filter disposed in a flow patch between said third and fourth openings, and
flow means for fluid interconnection with said fourth opening to deliver collected vital fluid therefrom, whereby fluids collected in said third sub-chamber effectively define a further fluid seal and vital fluid collected in said third sub-chamber may be continuously drawn from said fourth opening for reinfusion without introducing pressure irregularity in said third sub-chamber or interruption of said aspirating and collecting.

11. A vessel according to claim 10, wherein a said wall is transparent and the vessel further comprises an opaque mask defining a window array selectively positioned to display the volumes of filtered and unfiltered vital fluids collected in said third sub-chamber.

12. A vessel according to claim 11, wherein said window array further includes windows displaying portions of said water columns indicative of said first and second pressure differentials.

13. A vessel according to claim 12, further comprising a float ball in a said water column and visible through a window for indicating an anomalous suction condition in said third chamber.

14. A vessel according to claim 10, wherein said walls are constituted by two opposed wall pieces joined in a generally planar region and along generally linear strips within said planar region said two opposed wall pieces being assembled by linear vibration welding along said strips.

15. A vessel according to claim 10, wherein a said water column constitutes a manometer chamber having first and second branches communicating with said first and second openings, respectively, and wherein one of said branches is constituted by
   a first fluid body of a first cross-sectional area located in a direct air flow path between said first and second openings such that air bubbles pass through said first fluid body, and
   a second fluid body of second cross-sectional area in fluid communication with said first fluid body and located out of said air flow path such that air bubbles do not pass through said second fluid body,
   whereby airflow-induced evaporative loss from said manometer chamber is reduced thereby effecting more stable pressure regulation.

16. An improved system for the drainage and selective reinfusion of fluids from the thoracic cavity, of the type wherein the system includes a closed vessel having, in sequence, a manometer chamber for setting a desired vacuum underpressure, a water seal chamber, and a collection chamber, said collection chamber having an inlet port at an upper region thereof and a pooling sump at a lower region thereof, wherein the improvement comprises
   a gross filter in an open fluid path between said upper and lower regions for removing gross structures from thoracic cavity fluid aspirated through said inlet and means defining a temporary pooling region for said fluid as it travels to said pooling sump without obstructing flow from said inlet port,
   a closable transfer port defining an outflow path through an outer wall of said collection chamber at said sump, and
   suction compensation means for compensating bidirectional pressure changes in said collection chamber, so that thoracic fluid is collected and withdrawn along said outflow path for reinfusion from said transfer port without interrupting the aspiration of thoracic fluid through said inlet.

17. The improved system of claim 16, further comprising a transfer vessel attached to said transfer port, said transfer vessel including means within the transfer vessel for establishing a second vacuum underpressure, so that withdrawal of collected fluid is accomplished by a single line which interconnects said second vessel and said transfer port.

18. The improved system of claim 17, wherein the transfer vessel has a microporous vent so that fluids transferred to said transfer vessel may be gravity infused from said vessel without changing the volume of the vessel.

19. A disposable autoinfusion apparatus for the collection of fluids from the thoracic cavity of a patient and reinfusion thereof, said apparatus comprising
   a continuously aspirating collection unit comprising first, second and third serially-connected chambers wherein said first chamber includes vacuum setting means for connection to a vacuum source and setting of a desired underpressure, said second chamber includes a water seal interposed between said first and third chamber, and wherein said third chamber includes an inlet for fluid flow connection to the thoracic cavity, an outlet in fluid flow communication with said second chamber, a lower pooling region for the pooling of fluid aspirated through said inlet, and also includes first and second access ports at said pooling region, said first access port being adapted for aseptically withdrawing a fluid sample from said pooling region and said second access port defining a conduit opening at a subsurface level of said pooling region, a gross filter located across a first physical flow path between said inlet and said pooling region of said collection unit, and a barrier rising above said gross filter to define an overflow path for fluid impounded by said gross filter, and
   means for selectively drawing fluid from said second access port to reinfuse said fluid while maintaining said desired underpressure in said collection chamber, whereby said pooled fluid from said collection unit is reinfused without interrupting collection from the thoracic cavity.

20. The apparatus of claim 19, wherein said means for selectively drawing fluid comprises a drain tube for connecting said second access port to an infusion pump to reinfuse collected fluid from said pooling region.

21. The apparatus of claim 19, wherein said means for selectively drawing fluid comprises a flexible vessel attached to said second access port said flexible vessel having an interior spring mechanism effective to create an internal suction by bearing against the vessel walls, said flexible vessel further having a closeable microporous vent which allows the vessel when disconnected from the access port to be connected for gravity-infusion of its contents into a patient.

22. The apparatus of claim 19, wherein said first physical flow path and said overflow path each pass through a gross filter and are of different cross-sectional areas.

23. The apparatus of claim 22, further comprising a second barrier defining a third overflow path.

24. The apparatus of claim 22, further comprising means for displaying a filter status condition.

25. The apparatus of claim 24, wherein the filter status condition includes an indication of fluid back-up.

26. The apparatus of claim 19, wherein said third chamber includes an upper chamber including said inlet, a lower chamber including said second access port, and a gross filter defining a permeable barrier between said upper and lower chambers, said upper chamber further having a vertically extending wall defining an overflow opening for the passage of unfiltered fluid from the upper chamber when the gross filter is blocked, thereby preventing vacuum blockages and consequent obstruction of flow through said inlet.

* * * * *

UNITED STATES PATENT AND TRADEMARK OFFICE
CERTIFICATE OF CORRECTION

PATENT NO. : 4,988,342

DATED : January 29, 1991

INVENTOR(S) : Herweck et al.

It is certified that error appears in the above-identified patent and that said Letters Patent is hereby corrected as shown below:

Column 5, line 17, please replace "Port" with --port--.

Column 5, line 23, after "filter 24" please insert --,--.

Column 8, line 10, after "delivery" please insert --.--.

Column 10, line 50, please replace "he" with --the--.

Signed and Sealed this

Twentieth Day of October, 1992

Attest:

DOUGLAS B. COMER

*Attesting Officer*     *Acting Commissioner of Patents and Trademarks*